United States Patent
Zeng et al.

(10) Patent No.: US 8,669,360 B2
(45) Date of Patent: Mar. 11, 2014

(54) METHODS OF CONVERTING AMORPHOUS DRUG SUBSTANCE INTO CRYSTALLINE FORM

(75) Inventors: Maggie Zeng, Maple Grove, MN (US); Yen-Lane Chen, New Brighton, MN (US); Maura Romanshek, Buffalo, MN (US); Erin Meyer, Montrose, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 81 days.

(21) Appl. No.: 13/242,433

(22) Filed: Sep. 23, 2011

(65) Prior Publication Data

US 2013/0035483 A1 Feb. 7, 2013

Related U.S. Application Data

(60) Provisional application No. 61/515,500, filed on Aug. 5, 2011.

(51) Int. Cl.
*C07D 498/00* (2006.01)

(52) U.S. Cl.
USPC ........................................................ 540/456

(58) Field of Classification Search
USPC ........................................................ 540/456
See application file for complete search history.

(56) References Cited

U.S. PATENT DOCUMENTS

| | | |
|---|---|---|
| 304,121 A | 8/1884 | Munch |
| 4,026,296 A | 5/1977 | Stoy |
| 4,186,745 A | 2/1980 | Lewis |
| 4,364,392 A | 12/1982 | Strother |
| 4,481,323 A | 11/1984 | Sterling |
| 4,490,421 A | 12/1984 | Levy |
| 4,515,593 A | 5/1985 | Norton |
| 4,589,873 A | 5/1986 | Schwartz |
| 4,603,152 A | 7/1986 | Laurin |
| 4,644,936 A | 2/1987 | Schiff |
| 4,693,243 A | 9/1987 | Buras |
| 4,733,665 A | 3/1988 | Palmaz |
| 4,769,013 A | 9/1988 | Lorenz |
| 4,784,647 A | 11/1988 | Gross |
| 4,796,629 A | 1/1989 | Grayzel |
| 4,800,882 A | 1/1989 | Gianturco |
| 4,886,062 A | 12/1989 | Wiktor |
| 4,906,244 A | 3/1990 | Pinchuk |
| 4,931,583 A | 6/1990 | Hull |
| 4,950,239 A | 8/1990 | Gahara |
| 4,950,256 A | 8/1990 | Luther |
| 4,994,033 A | 2/1991 | Shockey |
| 5,026,607 A | 6/1991 | Kiezulas |
| 5,027,996 A | 7/1991 | Fefeu |
| 5,041,100 A | 8/1991 | Rowland |
| 5,049,131 A | 9/1991 | Deuss |
| 5,087,244 A | 2/1992 | Wolinsky |
| 5,091,205 A | 2/1992 | Fan |
| 2,098,381 A | 3/1992 | Schneider |
| 5,092,841 A | 3/1992 | Spears |
| 5,098,381 A | 3/1992 | Schneider |
| 5,102,402 A | 4/1992 | Dror |
| 5,135,516 A | 8/1992 | Sahatjian |
| 5,169,933 A | 12/1992 | Anderson |
| 5,180,366 A | 1/1993 | Woods |
| 5,199,951 A | 4/1993 | Spears |
| 5,213,576 A | 5/1993 | Abiuso |
| 5,213,580 A | 5/1993 | Slepian |
| 5,232,444 A | 8/1993 | Just |
| 5,236,413 A | 8/1993 | Feiring |
| 5,250,069 A | 10/1993 | Nobuyoshi |
| 5,264,260 A | 11/1993 | Saab |
| 5,270,086 A | 12/1993 | Hamlin |
| 5,282,785 A | 2/1994 | Shapland |
| 5,286,254 A | 2/1994 | Shapland |
| 5,295,962 A | 3/1994 | Crocker |
| 5,304,121 A | 4/1994 | Sahatjian |
| 5,318,531 A | 6/1994 | Leone |
| 5,320,634 A | 6/1994 | Vigil |
| 5,324,261 A | 6/1994 | Amundson |
| 5,328,468 A | 7/1994 | Kaneko |
| 5,328,471 A | 7/1994 | Slepian |
| 5,342,628 A | 8/1994 | Picha |
| 5,344,400 A | 9/1994 | Kaneko |
| 5,344,402 A | 9/1994 | Crocker |
| 5,362,831 A | 11/1994 | Mongelli |
| 5,368,566 A | 11/1994 | Crocker |
| 5,370,614 A | 12/1994 | Amundson |
| 5,380,299 A | 1/1995 | Fearnot |
| 5,383,928 A | 1/1995 | Scott |
| 5,385,152 A | 1/1995 | Abele |
| 5,405,472 A | 4/1995 | Leone |
| 5,419,760 A | 5/1995 | Narciso |
| 5,421,826 A | 6/1995 | Crocker |
| 5,425,703 A | 6/1995 | Feiring |
| 5,427,767 A | 6/1995 | Kresse |
| 5,439,446 A | 8/1995 | Barry |

(Continued)

FOREIGN PATENT DOCUMENTS

| | | |
|---|---|---|
| CA | 2363119 | 8/2000 |
| DE | 19908318 | 8/2000 |

(Continued)

OTHER PUBLICATIONS

Abstract from Liggins, R. T., Hunter, W. L and Burt, H. M. 'Solid-state characterization of paclitaxel.' Journal of Pharmaceutical Sciences, 86: 1458-1463, (1997).

(Continued)

*Primary Examiner* — Bruck Kifle

(74) *Attorney, Agent, or Firm* — Vidas, Arrett & Steinkraus, P.A.

(57) ABSTRACT

A method for converting an amorphous drug, such as everolimus, or other macrolide immunosuppressive drug, into a crystalline form. The method utilizes a slurry of the drug in organic liquid phase and ages the slurry to achieve the conversion.

9 Claims, 3 Drawing Sheets

(56) References Cited

U.S. PATENT DOCUMENTS

| | | |
|---|---|---|
| 5,443,496 A | 8/1995 | Schwartz |
| 5,447,724 A | 9/1995 | Helmus |
| 5,449,382 A | 9/1995 | Dayton |
| 5,464,650 A | 11/1995 | Berg |
| 5,470,307 A | 11/1995 | Lindall |
| 5,489,525 A | 2/1996 | Pastan |
| 5,498,238 A | 3/1996 | Shapland |
| 5,499,971 A | 3/1996 | Shapland |
| 5,500,180 A | 3/1996 | Anderson |
| 5,542,926 A | 8/1996 | Crocker |
| 5,545,208 A | 8/1996 | Wolff |
| 5,549,603 A | 8/1996 | Feiring |
| 5,554,119 A | 9/1996 | Harrison |
| 5,554,182 A | 9/1996 | Dinh |
| 5,556,383 A | 9/1996 | Wang |
| 5,558,642 A | 9/1996 | Schweich, Jr. |
| 5,562,922 A | 10/1996 | Lambert |
| 5,569,184 A | 10/1996 | Crocker |
| 5,569,463 A | 10/1996 | Helmus |
| 5,571,089 A | 11/1996 | Crocker |
| 5,578,075 A | 11/1996 | Dayton |
| 5,588,962 A | 12/1996 | Nicholas |
| 5,599,306 A | 2/1997 | Klein |
| 5,599,307 A | 2/1997 | Bacher |
| 5,609,629 A | 3/1997 | Fearnot |
| 5,611,775 A | 3/1997 | Machold |
| 5,616,149 A | 4/1997 | Barath |
| 5,624,411 A | 4/1997 | Tuch |
| 5,626,862 A | 5/1997 | Brem |
| 5,628,730 A | 5/1997 | Shapland |
| 5,629,008 A | 5/1997 | Lee |
| 5,634,901 A | 6/1997 | Alba |
| 5,637,086 A | 6/1997 | Ferguson |
| 5,651,986 A | 7/1997 | Brem |
| 5,665,772 A | 9/1997 | Cottens |
| 5,669,874 A | 9/1997 | Feiring |
| 5,674,192 A | 10/1997 | Sahatjian |
| 5,674,241 A | 10/1997 | Bley |
| 5,679,400 A | 10/1997 | Tuch |
| 5,685,847 A | 11/1997 | Barry |
| 5,688,516 A | 11/1997 | Raad |
| 5,693,034 A | 12/1997 | Buscemi |
| 5,697,967 A | 12/1997 | Dinh |
| 5,704,908 A | 1/1998 | Hofmann |
| 5,707,385 A | 1/1998 | Williams |
| 5,716,981 A | 2/1998 | Hunter |
| 5,728,066 A | 3/1998 | Daneshvar |
| 5,733,925 A | 3/1998 | Kunz |
| 5,766,158 A | 6/1998 | Opolski |
| 5,769,883 A | 6/1998 | Buscemi |
| 5,797,877 A | 8/1998 | Hamilton |
| 5,800,538 A | 9/1998 | Slepian |
| 5,807,306 A | 9/1998 | Shapland |
| 5,810,763 A | 9/1998 | Feiring |
| 5,833,657 A | 11/1998 | Reinhardt et al. |
| 5,833,658 A | 11/1998 | Levy |
| 5,843,089 A | 12/1998 | Sahatjian |
| 5,854,382 A | 12/1998 | Loomis |
| 5,855,546 A | 1/1999 | Hastings |
| 5,857,998 A | 1/1999 | Barry |
| 5,865,801 A | 2/1999 | Houser |
| 5,868,719 A | 2/1999 | Tsukernik |
| 5,869,127 A | 2/1999 | Zhong |
| 5,876,374 A | 3/1999 | Alba |
| 5,893,840 A | 4/1999 | Hull |
| 5,900,246 A | 5/1999 | Lambert |
| 5,902,266 A | 5/1999 | Leone |
| 5,902,299 A | 5/1999 | Jayaraman |
| 5,928,279 A | 7/1999 | Shannon |
| 5,935,275 A | 8/1999 | Burgard |
| 5,935,506 A | 8/1999 | Schmitz |
| 5,947,977 A | 9/1999 | Slepian |
| 5,954,693 A | 9/1999 | Barry |
| 5,954,706 A | 9/1999 | Sahatjian |
| 5,977,163 A | 11/1999 | Li |
| 5,981,568 A | 11/1999 | Kunz |
| 6,048,356 A | 4/2000 | Ravenscroft |
| 6,048,515 A | 4/2000 | Kresse |
| 6,048,620 A | 4/2000 | Zhong |
| 6,099,454 A | 8/2000 | Hastings |
| 6,099,926 A | 8/2000 | Thakrar |
| 6,129,705 A | 10/2000 | Grantz |
| 6,142,973 A | 11/2000 | Carleton |
| 6,146,356 A | 11/2000 | Wang et al. |
| 6,146,358 A | 11/2000 | Rowe |
| 6,183,658 B1 | 2/2001 | Lesniak |
| 6,186,745 B1 | 2/2001 | Johnson |
| 6,195,583 B1 | 2/2001 | Feiring |
| 6,203,551 B1 | 3/2001 | Wu |
| 6,218,016 B1 | 4/2001 | Tedeschi |
| 6,219,577 B1 | 4/2001 | Brown |
| 6,240,407 B1 | 5/2001 | Chang |
| 6,245,103 B1 | 6/2001 | Stinson |
| 6,262,107 B1 | 7/2001 | Li |
| 6,270,522 B1 | 8/2001 | Simhambhatla |
| 6,280,411 B1 | 8/2001 | Lennox |
| 6,283,947 B1 | 9/2001 | Mirzaee |
| 6,287,332 B1 | 9/2001 | Bolz |
| 6,296,619 B1 | 10/2001 | Brisken |
| 6,299,604 B1 | 10/2001 | Ragheb |
| 6,306,166 B1 | 10/2001 | Barry |
| 6,344,028 B1 | 2/2002 | Barry |
| 6,355,029 B1 | 3/2002 | Joye |
| 6,364,856 B1 | 4/2002 | Ding |
| 6,364,893 B1 | 4/2002 | Sahatjian |
| 6,369,039 B1 | 4/2002 | Palasis |
| 6,389,314 B2 | 5/2002 | Feiring |
| 6,391,033 B2 | 5/2002 | Ryan |
| 6,398,708 B1 | 6/2002 | Hastings |
| 6,409,716 B1 | 6/2002 | Sahatjian |
| 6,418,448 B1 | 7/2002 | Sarkar |
| 6,419,692 B1 | 7/2002 | Yang |
| 6,428,534 B1 | 8/2002 | Joye |
| 6,432,102 B2 | 8/2002 | Joye |
| 6,440,990 B1 | 8/2002 | Cottens |
| 6,443,941 B1 | 9/2002 | Slepian |
| 6,451,373 B1 | 9/2002 | Hossainy |
| 6,468,297 B1 | 10/2002 | Williams |
| 6,494,862 B1 | 12/2002 | Ray |
| 6,506,408 B1 | 1/2003 | Palasis |
| 6,511,477 B2 | 1/2003 | Altman |
| 6,514,245 B1 | 2/2003 | Williams |
| 6,524,274 B1 | 2/2003 | Rosenthal |
| 6,527,740 B1 | 3/2003 | Jackson |
| 6,537,194 B1 | 3/2003 | Winkler |
| 6,541,039 B1 | 4/2003 | Lesniak |
| 6,544,221 B1 | 4/2003 | Kokish |
| 6,544,223 B1 | 4/2003 | Kokish |
| 6,545,097 B2 | 4/2003 | Pinchuk |
| 6,548,569 B1 | 4/2003 | Williams |
| 6,582,353 B1 | 6/2003 | Hastings |
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien |
| 6,623,749 B2 | 9/2003 | Williams |
| 6,638,246 B1 | 10/2003 | Naimark |
| 6,645,135 B1 | 11/2003 | Bhat |
| 6,648,879 B2 | 11/2003 | Joye |
| 6,656,156 B2 | 12/2003 | Yang |
| 6,663,880 B1 | 12/2003 | Roorda |
| 6,682,545 B1 | 1/2004 | Kester |
| 6,685,648 B2 | 2/2004 | Flaherty |
| 6,699,272 B2 | 3/2004 | Slepian |
| 6,706,013 B1 | 3/2004 | Bhat |
| 6,730,105 B2 | 5/2004 | Shiber |
| 6,733,474 B2 | 5/2004 | Kusleika |
| 6,780,324 B2 | 8/2004 | Le Garrec |
| 6,783,543 B2 | 8/2004 | Jang |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta |

(56) References Cited

U.S. PATENT DOCUMENTS

| | | |
|---|---|---|
| 6,805,898 B1 | 10/2004 | Wu |
| 6,811,550 B2 | 11/2004 | Holland |
| 6,838,493 B2 | 1/2005 | Williams |
| 6,858,644 B2 | 2/2005 | Benigni |
| 6,863,861 B1 | 3/2005 | Zhang (Ken) |
| 6,867,247 B2 | 3/2005 | Williams |
| 6,890,339 B2 | 5/2005 | Sahatjian |
| 6,890,583 B2 | 5/2005 | Chudzik |
| 6,899,731 B2 | 5/2005 | Li |
| 6,908,462 B2 | 6/2005 | Joye |
| 6,918,927 B2 | 7/2005 | Bates |
| 6,923,996 B2 | 8/2005 | Epstein |
| 6,939,320 B2 | 9/2005 | Lennox |
| 6,942,680 B2 | 9/2005 | Grayzel |
| 6,955,661 B1 | 10/2005 | Herweck |
| 6,960,346 B2 | 11/2005 | Shukla |
| 6,972,015 B2 | 12/2005 | Joye |
| 6,991,647 B2 | 1/2006 | Jadhav |
| 7,005,414 B2 | 2/2006 | Barnikol |
| 7,008,979 B2 | 3/2006 | Schottman |
| 7,018,371 B2 | 3/2006 | Forman |
| 7,037,319 B2 | 5/2006 | Weber |
| 7,048,714 B2 | 5/2006 | Richter |
| 7,056,533 B2 | 6/2006 | Chudzik |
| 7,060,051 B2 | 6/2006 | Palasis |
| 7,060,062 B2 | 6/2006 | Joye |
| 7,066,904 B2 | 6/2006 | Rosenthal |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | Mc Hale |
| 7,166,098 B1 | 1/2007 | Steward |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford |
| 7,323,189 B2 | 1/2008 | Pathak |
| 7,335,184 B2 | 2/2008 | Laguna |
| 7,357,940 B2 | 4/2008 | Richard |
| 7,364,585 B2 | 4/2008 | Weber |
| 7,371,257 B2 | 5/2008 | Sahatjian |
| 7,381,418 B2 | 6/2008 | Richard |
| 7,393,685 B1 | 7/2008 | Jordan |
| 7,402,172 B2 | 7/2008 | Chin |
| 7,407,671 B2 | 8/2008 | McBride |
| 7,407,684 B2 | 8/2008 | Spencer |
| 7,459,169 B2 | 12/2008 | Nilsson |
| 7,462,165 B2 | 12/2008 | Ding |
| 7,470,252 B2 | 12/2008 | Mickley |
| 7,473,242 B2 | 1/2009 | Donovan |
| 7,491,188 B2 | 2/2009 | Holman |
| 7,494,497 B2 | 2/2009 | Weber |
| 7,527,604 B2 | 5/2009 | Naimark |
| 7,553,292 B2 | 6/2009 | Kilpatrick |
| 7,563,324 B1 | 7/2009 | Chen |
| 7,572,245 B2 | 8/2009 | Herweck |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze |
| 7,718,213 B1 | 5/2010 | Scheer |
| 7,731,685 B2 | 6/2010 | Ragheb |
| 7,744,644 B2 | 6/2010 | Weber |
| 7,750,041 B2 | 7/2010 | Speck |
| 7,753,876 B2 | 7/2010 | Cervantes |
| 7,758,892 B1 | 7/2010 | Chen |
| 7,762,995 B2 | 7/2010 | Eversull |
| 7,767,219 B2 | 8/2010 | Weber |
| 7,771,740 B2 | 8/2010 | Strickler |
| 7,773,447 B2 | 8/2010 | Kajigaya |
| 7,794,751 B2 | 9/2010 | Chudzik |
| 7,803,149 B2 | 9/2010 | Bates |
| 7,811,622 B2 | 10/2010 | Bates |
| 8,291,854 B2 | 10/2012 | Behnisch |
| 2001/0020151 A1 | 9/2001 | Reed |
| 2002/0010489 A1 | 1/2002 | Grayzel |
| 2002/0037358 A1 | 3/2002 | Barry |
| 2002/0041898 A1 | 4/2002 | Unger |
| 2002/0042645 A1 | 4/2002 | Shannon |
| 2002/0151844 A1 | 10/2002 | Yang |
| 2002/0183581 A1 | 12/2002 | Yoe |
| 2003/0028210 A1 | 2/2003 | Boyle |
| 2003/0040712 A1 | 2/2003 | Ray |
| 2003/0060877 A1 | 3/2003 | Falotico |
| 2003/0064965 A1 | 4/2003 | Richter |
| 2003/0077253 A1 | 4/2003 | Palasis |
| 2003/0083740 A1 | 5/2003 | Pathak |
| 2003/0114791 A1 | 6/2003 | Rosenthal |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz |
| 2003/0236514 A1 | 12/2003 | Schwarz |
| 2004/0023851 A1 | 2/2004 | Barnikol |
| 2004/0033251 A1 | 2/2004 | Sparer |
| 2004/0034336 A1 | 2/2004 | Scott |
| 2004/0039437 A1 | 2/2004 | Sparer |
| 2004/0044308 A1 | 3/2004 | Naimark |
| 2004/0044404 A1 | 3/2004 | Stucke |
| 2004/0047911 A1 | 3/2004 | Lyu |
| 2004/0059290 A1 | 3/2004 | Palasis |
| 2004/0064093 A1 | 4/2004 | Hektner |
| 2004/0073284 A1 | 4/2004 | Bates |
| 2004/0077948 A1 | 4/2004 | Violante |
| 2004/0086569 A1 | 5/2004 | Sparer |
| 2004/0098014 A1 | 5/2004 | Flugelman |
| 2004/0098108 A1 | 5/2004 | Harder |
| 2004/0111144 A1 | 6/2004 | Lawin |
| 2004/0115273 A1 | 6/2004 | Sparer |
| 2004/0117222 A1 | 6/2004 | Rokosz |
| 2004/0127978 A1 | 7/2004 | Sparer |
| 2004/0137066 A1 | 7/2004 | Jayaraman |
| 2004/0142011 A1 | 7/2004 | Nilsson |
| 2004/0143287 A1 | 7/2004 | Konstantino |
| 2004/0175406 A1 | 9/2004 | Schwarz |
| 2004/0180039 A1 | 9/2004 | Toner |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett |
| 2004/0224003 A1 | 11/2004 | Schultz |
| 2004/0224080 A1 | 11/2004 | Epstein |
| 2004/0230176 A1 | 11/2004 | Shanahan |
| 2004/0234575 A1 | 11/2004 | Horres |
| 2004/0260239 A1 | 12/2004 | Kusleika |
| 2005/0015046 A1 | 1/2005 | Weber |
| 2005/0025801 A1 | 2/2005 | Richard |
| 2005/0025802 A1 | 2/2005 | Richard |
| 2005/0025803 A1 | 2/2005 | Richard |
| 2005/0025848 A1 | 2/2005 | Huang |
| 2005/0027283 A1 | 2/2005 | Richard |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco |
| 2005/0060028 A1 | 3/2005 | Horres |
| 2005/0064005 A1 | 3/2005 | Dinh |
| 2005/0064038 A1 | 3/2005 | Dinh |
| 2005/0101522 A1 | 5/2005 | Speck |
| 2005/0106206 A1 | 5/2005 | Herweck |
| 2005/0129727 A1 | 6/2005 | Weber |
| 2005/0129731 A1 | 6/2005 | Horres |
| 2005/0154416 A1 | 7/2005 | Herweck |
| 2005/0158359 A1 | 7/2005 | Epstein |
| 2005/0169969 A1 | 8/2005 | Li |
| 2005/0176678 A1 | 8/2005 | Horres |
| 2005/0181015 A1 | 8/2005 | Zhong |

(56) References Cited

U.S. PATENT DOCUMENTS

| | | |
|---|---|---|
| 2005/0182361 A1 | 8/2005 | Lennox |
| 2005/0209548 A1 | 9/2005 | Dev |
| 2005/0215722 A1 | 9/2005 | Pinchunk |
| 2005/0220853 A1 | 10/2005 | Dao |
| 2005/0222677 A1 | 10/2005 | Bates |
| 2005/0226991 A1 | 10/2005 | Hossainy |
| 2005/0233061 A1 | 10/2005 | Schwarz |
| 2005/0244456 A1 | 11/2005 | Nilsson |
| 2005/0244459 A1 | 11/2005 | DeWitt |
| 2005/0246009 A1 | 11/2005 | Toner |
| 2005/0251106 A1 | 11/2005 | Cervantes |
| 2005/0273049 A1 | 12/2005 | Krulevitch |
| 2005/0273075 A1 | 12/2005 | Krulevitch |
| 2005/0278021 A1 | 12/2005 | Bates |
| 2005/0288629 A1 | 12/2005 | Kunis |
| 2006/0002968 A1 | 1/2006 | Stewart |
| 2006/0002973 A1 | 1/2006 | Barry |
| 2006/0013853 A1 | 1/2006 | Richard |
| 2006/0013854 A1 | 1/2006 | Strickler |
| 2006/0020243 A1 | 1/2006 | Speck |
| 2006/0020331 A1 | 1/2006 | Bates |
| 2006/0025848 A1 | 2/2006 | Weber |
| 2006/0041225 A1 | 2/2006 | Wallace |
| 2006/0057208 A1 | 3/2006 | Holzer |
| 2006/0058815 A1 | 3/2006 | Mickley |
| 2006/0067977 A1 | 3/2006 | Labrecque |
| 2006/0079836 A1 | 4/2006 | Holman |
| 2006/0083768 A1 | 4/2006 | Labrecque |
| 2006/0085058 A1 | 4/2006 | Rosenthal |
| 2006/0088566 A1 | 4/2006 | Parsonage |
| 2006/0088596 A1 | 4/2006 | Labrecque |
| 2006/0112536 A1 | 6/2006 | Herweck |
| 2006/0121081 A1 | 6/2006 | Labrecque |
| 2006/0121088 A1 | 6/2006 | Hunter |
| 2006/0129093 A1 | 6/2006 | Jackson |
| 2006/0134160 A1 | 6/2006 | Troczynski |
| 2006/0134168 A1 | 6/2006 | Chappa |
| 2006/0135548 A1 | 6/2006 | Keri |
| 2006/0147491 A1 | 7/2006 | DeWitt |
| 2006/0165754 A1 | 7/2006 | Ranade |
| 2006/0167407 A1 | 7/2006 | Weber |
| 2006/0171982 A1 | 8/2006 | Timm |
| 2006/0171984 A1 | 8/2006 | Cromack |
| 2006/0171985 A1 | 8/2006 | Richard |
| 2006/0184112 A1 | 8/2006 | Horn |
| 2006/0190022 A1 | 8/2006 | Beyar |
| 2006/0193890 A1 | 8/2006 | Owens |
| 2006/0193891 A1 | 8/2006 | Richard |
| 2006/0195176 A1 | 8/2006 | Bates |
| 2006/0200048 A1 | 9/2006 | Furst |
| 2006/0200556 A1 | 9/2006 | Brave |
| 2006/0204537 A1 | 9/2006 | Ratner |
| 2006/0212106 A1 | 9/2006 | Weber |
| 2006/0224115 A1 | 10/2006 | Willard |
| 2006/0228452 A1 | 10/2006 | Cromack |
| 2006/0240070 A1 | 10/2006 | Cromack |
| 2006/0280858 A1 | 12/2006 | Kokish |
| 2006/0286071 A1 | 12/2006 | Epstein |
| 2006/0286141 A1 | 12/2006 | Campbell |
| 2007/0003599 A1 | 1/2007 | Schwarz |
| 2007/0020307 A1 | 1/2007 | Zhong |
| 2007/0027523 A1 | 2/2007 | Toner |
| 2007/0067882 A1 | 3/2007 | Atanasoska |
| 2007/0078413 A1 | 4/2007 | Stenzel |
| 2007/0083149 A1 | 4/2007 | Steward |
| 2007/0088246 A1 | 4/2007 | Steward |
| 2007/0088255 A1 | 4/2007 | Toner |
| 2007/0093745 A1 | 4/2007 | Steward |
| 2007/0104766 A1 | 5/2007 | Wang |
| 2007/0106250 A1 | 5/2007 | Seward |
| 2007/0106363 A1 | 5/2007 | Weber |
| 2007/0112330 A1 | 5/2007 | Palasis |
| 2007/0129474 A1 | 6/2007 | Salamone |
| 2007/0129792 A1 | 6/2007 | Picart |
| 2007/0150465 A1 | 6/2007 | Brave |
| 2007/0150466 A1 | 6/2007 | Brave |
| 2007/0150470 A1 | 6/2007 | Brave |
| 2007/0150515 A1 | 6/2007 | Brave |
| 2007/0150646 A1 | 6/2007 | Yoon |
| 2007/0154554 A1 | 7/2007 | Burgermeister |
| 2007/0178136 A1 | 8/2007 | Arney |
| 2007/0185561 A1 | 8/2007 | Schmitz |
| 2007/0212386 A1 | 9/2007 | Patravale |
| 2007/0212387 A1 | 9/2007 | Patravale |
| 2007/0212393 A1 | 9/2007 | Patravale |
| 2007/0212394 A1 | 9/2007 | Reyes |
| 2007/0224234 A1 | 9/2007 | Steckel |
| 2007/0225800 A1 | 9/2007 | Sahatjian |
| 2007/0232996 A1 | 10/2007 | Andersen |
| 2007/0244548 A1 | 10/2007 | Myers |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2008/0020013 A1 | 1/2008 | Reyes |
| 2008/0021385 A1 | 1/2008 | Barry |
| 2008/0027421 A1 | 1/2008 | Vancelette |
| 2008/0031173 A1 | 2/2008 | Zhang |
| 2008/0040314 A1 | 2/2008 | Brave |
| 2008/0050415 A1 | 2/2008 | Atanasoska |
| 2008/0051541 A1 | 2/2008 | Strickler |
| 2008/0057102 A1 | 3/2008 | Roorda |
| 2008/0071350 A1 | 3/2008 | Stinson |
| 2008/0071358 A1 | 3/2008 | Weber |
| 2008/0089958 A1 | 4/2008 | Diehl |
| 2008/0091008 A1 | 4/2008 | Viswanath |
| 2008/0095847 A1 | 4/2008 | Glauser |
| 2008/0102033 A1 | 5/2008 | Speck |
| 2008/0102034 A1 | 5/2008 | Speck |
| 2008/0104004 A1 | 5/2008 | Brave |
| 2008/0113081 A1 | 5/2008 | Hossainy |
| 2008/0114331 A1 | 5/2008 | Holman |
| 2008/0118544 A1 | 5/2008 | Wang |
| 2008/0132992 A1 | 6/2008 | Bates |
| 2008/0140002 A1 | 6/2008 | Ramzipoor |
| 2008/0145396 A1 | 6/2008 | Bates |
| 2008/0145398 A1 | 6/2008 | Bates |
| 2008/0157444 A1 | 7/2008 | Melsheimer |
| 2008/0171129 A1 | 7/2008 | Ranade |
| 2008/0175887 A1 | 7/2008 | Wang |
| 2008/0195042 A1 | 8/2008 | Weber |
| 2008/0195079 A1 | 8/2008 | Moore |
| 2008/0199506 A1 | 8/2008 | Horres |
| 2008/0206304 A1 | 8/2008 | Lindquist |
| 2008/0208182 A1 | 8/2008 | Lafontaine |
| 2008/0220041 A1 | 9/2008 | Brito |
| 2008/0249464 A1 | 10/2008 | Spencer |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber |
| 2008/0311173 A1 | 12/2008 | Schwarz |
| 2009/0005849 A1 | 1/2009 | Hossainy |
| 2009/0018501 A1 | 1/2009 | Yribarren |
| 2009/0024200 A1 | 1/2009 | Wilcox |
| 2009/0047414 A1 | 2/2009 | Corbeil |
| 2009/0048667 A1 | 2/2009 | Mochizuki |
| 2009/0054837 A1 | 2/2009 | Von Holst |
| 2009/0069883 A1 | 3/2009 | Ding |
| 2009/0076448 A1 | 3/2009 | Consigny |
| 2009/0088735 A1 | 4/2009 | Abboud |
| 2009/0098176 A1 | 4/2009 | Helmus |
| 2009/0105686 A1 | 4/2009 | Snow |
| 2009/0105687 A1 | 4/2009 | Deckman |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates |
| 2009/0187144 A1 | 7/2009 | Jayaraman |
| 2009/0192537 A1 | 7/2009 | Obrien |
| 2009/0204082 A1 | 8/2009 | Wesselmann |
| 2009/0226502 A1 | 9/2009 | Chen |

(56) References Cited

U.S. PATENT DOCUMENTS

| | | |
|---|---|---|
| 2009/0227948 A1 | 9/2009 | Chen |
| 2009/0227949 A1 | 9/2009 | Knapp |
| 2009/0227980 A1 | 9/2009 | Kangas |
| 2009/0246252 A1 | 10/2009 | Arps |
| 2009/0254063 A1 | 10/2009 | Oepen |
| 2009/0258049 A1 | 10/2009 | Klein |
| 2009/0276036 A1 | 11/2009 | Nagura |
| 2009/0299355 A1 | 12/2009 | Bencini |
| 2009/0299356 A1 | 12/2009 | Watson |
| 2009/0318848 A1 | 12/2009 | Shippy, III |
| 2010/0010470 A1 | 1/2010 | Bates |
| 2010/0015200 A1 | 1/2010 | Mcclain |
| 2010/0023108 A1 | 1/2010 | Toner |
| 2010/0030183 A1 | 2/2010 | Toner |
| 2010/0036585 A1 | 2/2010 | Scharfenberg |
| 2010/0049294 A1 | 2/2010 | Zukowski |
| 2010/0049296 A1 | 2/2010 | Sarasam |
| 2010/0049309 A1 | 2/2010 | Bates |
| 2010/0055294 A1 | 3/2010 | Wang |
| 2010/0056985 A1 | 3/2010 | Weber |
| 2010/0063585 A1 | 3/2010 | Hoffmann |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber |
| 2010/0092540 A1 | 4/2010 | Pinchuk |
| 2010/0096781 A1 | 4/2010 | Huang |
| 2010/0125239 A1 | 5/2010 | Perry |
| 2010/0131043 A1 | 5/2010 | Casas |
| 2010/0145266 A1 | 6/2010 | Orlowski |
| 2010/0179475 A1 | 7/2010 | Hoffmann |
| 2010/0198190 A1 | 8/2010 | Michal |
| 2010/0209471 A1 | 8/2010 | Weber |
| 2010/0209473 A1 | 8/2010 | Dhont |
| 2010/0228333 A1 | 9/2010 | Drasler |
| 2010/0233228 A1 | 9/2010 | Speck |
| 2010/0233236 A1 | 9/2010 | Zhao |
| 2010/0239635 A1 | 9/2010 | McClain |
| 2010/0249702 A1 | 9/2010 | Magana |
| 2010/0256748 A1 | 10/2010 | Taylor |
| 2010/0261662 A1 | 10/2010 | Schreck |
| 2010/0268191 A1 | 10/2010 | Trudel |
| 2010/0272773 A1 | 10/2010 | Kangas |
| 2010/0272778 A1 | 10/2010 | McClain |
| 2010/0285085 A1 | 11/2010 | Stankus |
| 2010/0292641 A1 | 11/2010 | Wijay |
| 2010/0298769 A1 | 11/2010 | Schewe |
| 2010/0312182 A1 | 12/2010 | Adden |
| 2010/0318020 A1 | 12/2010 | Atanasoska |
| 2010/0324645 A1 | 12/2010 | Stankus |
| 2010/0324648 A1 | 12/2010 | Scheller |
| 2010/0331816 A1 | 12/2010 | Dadino |
| 2010/0331947 A1 | 12/2010 | Shalev |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas |
| 2011/0054443 A1 | 3/2011 | Weber |
| 2011/0087191 A1 | 4/2011 | Scheuermann |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0190864 A1 | 8/2011 | McClain |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0059316 A1 | 3/2012 | Owens |
| 2012/0078227 A1 | 3/2012 | Kangas |
| 2012/0095396 A1 | 4/2012 | Radhakrishnan |
| 2012/0231037 A1 | 9/2012 | Levi |
| 2013/0035483 A1 | 2/2013 | Zeng |
| 2013/0053947 A1 | 2/2013 | Kangas |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |
| EP | 0568310 | 11/1993 |
| EP | 0734721 | 3/1996 |
| EP | 0747069 | 4/1996 |
| EP | 0519063 | 5/1996 |
| EP | 0717041 | 6/1996 |
| EP | 0770401 | 5/1997 |
| EP | 0633796 | 11/1997 |
| EP | 0937469 | 8/1999 |
| EP | 0950386 | 10/1999 |
| EP | 0623354 | 10/2002 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1666071 | 8/2007 |
| EP | 1666070 | 9/2007 |
| EP | 1857127 | 11/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| EP | 2241341 | 1/2011 |
| GB | 2112646 | 7/1983 |
| GB | 2127839 | 9/1983 |
| JP | 663145 A | 3/1994 |
| JP | 2002240847 | 8/2002 |
| RU | 200513564 | 4/2004 |
| WO | 8912478 | 12/1989 |
| WO | 9108790 | 6/1991 |
| WO | 9211896 | 7/1992 |
| WO | 9215286 | 9/1992 |
| WO | 9306792 | 4/1993 |
| WO | 9421308 | 9/1994 |
| WO | 9423787 | 10/1994 |
| WO | 9503036 | 2/1995 |
| WO | 9503083 | 2/1995 |
| WO | 9508305 | 3/1995 |
| WO | 9521636 | 8/1995 |
| WO | 9625176 | 8/1996 |
| WO | 9632907 | 10/1996 |
| WO | 9639949 | 12/1996 |
| WO | 9710011 | 3/1997 |
| WO | 9725085 | 7/1997 |
| WO | 9733552 | 9/1997 |
| WO | 9741916 | 11/1997 |
| WO | 9831415 | 7/1998 |
| WO | 9901458 | 1/1999 |
| WO | 9908729 | 2/1999 |
| WO | 9916500 | 4/1999 |
| WO | 9925336 | 5/1999 |
| WO | 9929353 | 6/1999 |
| WO | 0032238 | 6/2000 |
| WO | 0032267 | 6/2000 |
| WO | 0045744 | 8/2000 |
| WO | 0149358 | 7/2001 |

(56) References Cited

FOREIGN PATENT DOCUMENTS

| WO | 0160441 | 8/2001 |
|---|---|---|
| WO | 0238065 | 5/2002 |
| WO | 0243796 | 6/2002 |
| WO | 02076509 | 10/2002 |
| WO | 03022265 | 3/2003 |
| WO | 03026718 | 4/2003 |
| WO | 03059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2006036970 | 4/2006 |
| WO | 2006039237 | 4/2006 |
| WO | 2006102359 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007090382 | 8/2007 |
| WO | 2007090385 | 8/2007 |
| WO | 2008003298 | 1/2008 |
| WO | 2008014222 | 1/2008 |
| WO | 2008045228 | 4/2008 |
| WO | 2008086794 | 7/2008 |
| WO | 2008089730 | 7/2008 |
| WO | 2008101486 | 8/2008 |
| WO | 2007109114 | 9/2008 |
| WO | 2008109114 | 9/2008 |
| WO | 2008125890 | 10/2008 |
| WO | 2008137237 | 11/2008 |
| WO | 2009002855 | 12/2008 |
| WO | 2009014692 | 1/2009 |
| WO | 2009018816 | 2/2009 |
| WO | 2009026914 | 3/2009 |
| WO | 2009036118 | 3/2009 |
| WO | 2009036135 | 3/2009 |
| WO | 2009066330 | 5/2009 |
| WO | 2009096822 | 8/2009 |
| WO | 2009100394 | 8/2009 |
| WO | 2009120361 | 10/2009 |
| WO | 2009121565 | 10/2009 |
| WO | 2009135125 | 11/2009 |
| WO | 2010009335 | 1/2010 |
| WO | 2010021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010146096 | 12/2010 |
| WO | 2010147805 | 12/2010 |
| WO | 2011009096 | 1/2011 |
| WO | 2011028419 | 3/2011 |
| WO | 2011097103 | 8/2011 |

OTHER PUBLICATIONS

Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.

Alexis et al., 'In vitro study of release mechanisms of paclitaxel and rapamycin from drug-incorporated biodegradable stent matrices' Journal of Controlled Release 98 (2004) 67-74.
Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.
Axel De Labriolle et al., "Paclitaxel-eluting balloon: From bench to bed", Catheterization and Cardiovascular Interventions, vol. 73. No. 5, Apr. 1, 2009, pp. 643-652.
Buvardi, S., et al., 'Merck Index', 1996, Merck and Co., p. 144.
Cardiovascular and Interventional Radiology, Supplement 1, Sep. 28-Oct. 2, 1997, 158-161.
Charles et al.; 'Ceramide-Coated Balloon Catheters Limit Neointimal Hyperplasia After Stretch Injury in Carotid Arteries' Circ. Res. 2000;87;282-288.
Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.
Cortese et al., "Paclitaxel-coated balloon versus drug-eluting stent during PCI of small coronary vessels, a prospective randomised clinical trial. The PICCOLETO Study", Heart 2010; 96:1291-1296.
Finkelstein et al., "Local Drug Delivery via a Coronary Stent with Programmable Release Pharmocokinetics," 2003, Circulation, 107, 777-784.
International Preliminary Report on Patentability of International Application No. PCT/DE20071001173 dated Aug. 4, 2009.
J. Wohrle et al., 'Comparison of the heparin coated vs the uncoated Jostent no influence on restenosis or clinical outcome' European Heart Journal, 2001, vol. 22, pp. 1808-1816.
Mastropaolo et al.; 'Crystal and molecular structure of paclitaxel (taxol)' Proc. Natl. Acad. Sci. USA vol. 92, pp. 6920-6924, Jul. 1995.
Partial European Search Report in EP 07005256.8, dated Jan. 25, 2008.
PCT/US 08/72660 Search Report, Nov. 6, 2008.
PCT/US 2005/47235 Search Report, Dec. 28, 2005.
Presentation by Dr. Cortese, "Paclitaxel-eluting balloon versus paclitaxel-eluting stent in small coronary vessel disease." The Piccoleto Trial (2010).
U.S. Appl. No. 61/322,451, filed Apr. 9, 2010.
U.S. Appl. No. 61/330,201, filed Apr. 30, 2010.
U.S. Appl. No. 61/332,544, filed Apr. 9, 2010.
U.S. Appl. No. 61/352,117, filed Jun. 7, 2010.
U.S. Appl. No. 61/379,608, filed Sep. 2, 2010.
U.S. Appl. No. 61/385,849, filed Sep. 23, 2010.
U.S. Appl. No. 61/394,104, filed Oct. 18, 2010.
U.S. Appl. No. 61/421,054, filed Dec. 8, 2010.
Scheller et al., "Treatment of Coronary In-Stent Restenosis with a Paclitaxel-Coated Balloon Catheter", The New England Journal of Medicine, 2006; 355:2113-24.
Scollott, S.J., et al., Taxol Inhibits Neointimal Smooth Muscle Cell Accumulation after Angioplasty in the Rat, 1995, Journal of Clinical Investigation, 95, pp. 1869-1876.
Westedt et al., "Paclitaxel releasing films consisting of poly(vinyl alcohol)-graft-poly(lactide-co-glycolide) and their potential as biodegradable stent coatings." 2006, J Control Release 111, 235-46 (abstract).
Written Opinion for PCT/DE2008/000096, (2008).
Xu et al., "Lactic-co-glycolic acid polymer with rapamycin coated stent reduces neo-intimal formation in a porcine coronary model", Journal of Clinical Cardiology, 2004, abstract.
Dowding et al., "Preparation and Swelling Properties of Poly(NIPAM) "Minigel" Particles Prepared by Inverse Suspension Polymerization," Journal of Colloid and Interface Science 221, 268-272 (2000).
Panda et al., "Synthesis and swelling characteristics of poly(N-isopropylacrylamide) temperature sensitive hydrogels crosslinked by electron beam irradiation," Radiation Physics and Chemistry 58 (2000) 101-110.
U.S. Appl. No. 61/394,104, filed Oct. 18, 2010; Inventor: Radhakrishnan et al.
Scheller et al., "A further alternative; Balloons can be coated, as well" Newsletter from annual meeting in DGK Apr. 21, 2006.
Mondesire (Targeting Mammalian Target of Rapamycin Synergistically Enhances Chemotherapy-Induced Cytotoxicity in Breast Cancer Cells, 10 Clin. Cancer Res. 7031 (2004).
U.S. Appl. No. 61/271,167, filed Jul. 17, 2009.
U.S. Appl. No. 61/527,203, filed Aug. 25, 2011.
PCT Search Report and Written Opinion for PCT/US2011/052935.

METHODS OF CONVERTING AMORPHOUS DRUG SUBSTANCE INTO CRYSTALLINE FORM

CROSS-REFERENCE TO RELATED APPLICATIONS

This application claims the benefit of U.S. Provisional Application No. 61/515,500, entitled, "METHODS OF CONVERTING AMORPHOUS DRUG SUBSTANCE INTO CRYSTALLINE FORM," by Maggie Zeng, Yen-Lane Chen, Maura Romanshek, and Erin Meyer, and filed on Aug. 5, 2011, the entire contents of which being incorporated herein by reference.

BACKGROUND OF THE INVENTION

Commercial everolimus, as supplied by the manufacturer Novartis, is an amorphous solid that has a high bioavailability. A crystalline form exists which has a lower water solubility.

U.S. Pat. No. 7,232,486 describes a method for crystallizing tacrolimius that is said to work with everolimus as well. The method uses a polar solvent solution of the drug that is combined with a 2-phase hydrocarbon and aqueous system. The drug is entirely dissolved in the polar solvent. Controlled pH of the aqueous phase is understood to be important in this method.

SUMMARY OF THE INVENTION

The present invention pertains to a method for converting an amorphous drug, such as everolimus, tacrolimus, sirolimus, zotarolimus, biolimus, rapamycin or other macrolide immunosuppressive drug, into a crystalline form. In some embodiments the invention pertains specifically to conversion of everolimus.

The method utilizes slurry of the drug in organic liquid to achieve conversion with high efficiency.

In some aspects the inventive method comprises the steps of providing an amount of a drug in a solid amorphous form;
providing a volume of a solvent for the drug, the volume being insufficient to fully dissolve said amount of the drug;
forming a slurry with said volume of said solvent and said amount of said drug; and
aging the slurry for a time to allow substantial conversion of the solid amorphous drug into crystalline drug.

In some embodiments the slurry is continuously or intermittently subjected to agitation.

In some embodiments the solvent is cooled or partially evaporated after a period of time to form seed crystal.

Further aspects pertain to medical devices comprising polymer-free drug coating comprising a crystalline drug with or without a protective polymer layer thereover. In some embodiments no protective layer is needed. In some embodiments the drug is everolimus.

These and other aspects and embodiments of the invention are described in the Detailed Description, Claims and Figures which follow.

DETAILED DESCRIPTION OF THE INVENTION

The invention provides a simple cost effective method of conversion from amorphous drug to crystalline drug.

Drug morphology has significant impact on drug release kinetics and bioavailability of the drug product. While drug in amorphous solid state may be desirable for some applications where high dissolution rates and quick adsorption are required, the amorphous materials tend to exist in metastable states that may be prone to chemical and physical instability. Previous work done on drug-eluting-balloons have demonstrated that a sustained paclitaxel tissue concentration can be achieved by controlling appropriate drug morphology between various polymorphs of that drug.

While the amorphous form of some drug substances such as everolimus are generally suited for conventional administration routes, and in some cases have also been successfully used in compositions with polymers on stents for prevention of restenosis, the crystalline forms of such drugs are of particular importance for use in anti-restenotic drug coatings, for instance, in coatings on stents that provide extended tissue residence times on the stent without using a polymer. The crystalline forms are also of interest for delivery from balloons or at the site of balloon deployment, and on other medical devices.

The inventors hereof have discovered, for instance, that amorphous everolimus can be readily converted into crystalline form in very high yield using single-phase organic solvent systems from slurries of the amorphous drug. Solubility of the crystalline everolimus is about 25 times lower than that of amorphous everolimus, which confirms the suitability of using crystalline everolimus to achieve sustained tissue concentration in drug delivery products. This crystalline form is especially useful for achieving controlled and sustained drug release for polymer-free drug eluting stents and polymer-free drug eluting balloons, where no polymer matrix is present in the coating to modulate the drug release.

Everolimus is manufactured and supplied by Novartis as the amorphous form drug. It is the active agent used in the drug eluting stent coating of the PROMUS® Element® and Ion™ drug eluting stent systems sold by Boston Scientific Inc. It remains in amorphous state in that coating and the drug release from that stent is controlled by a polymer matrix.

Figure 1:
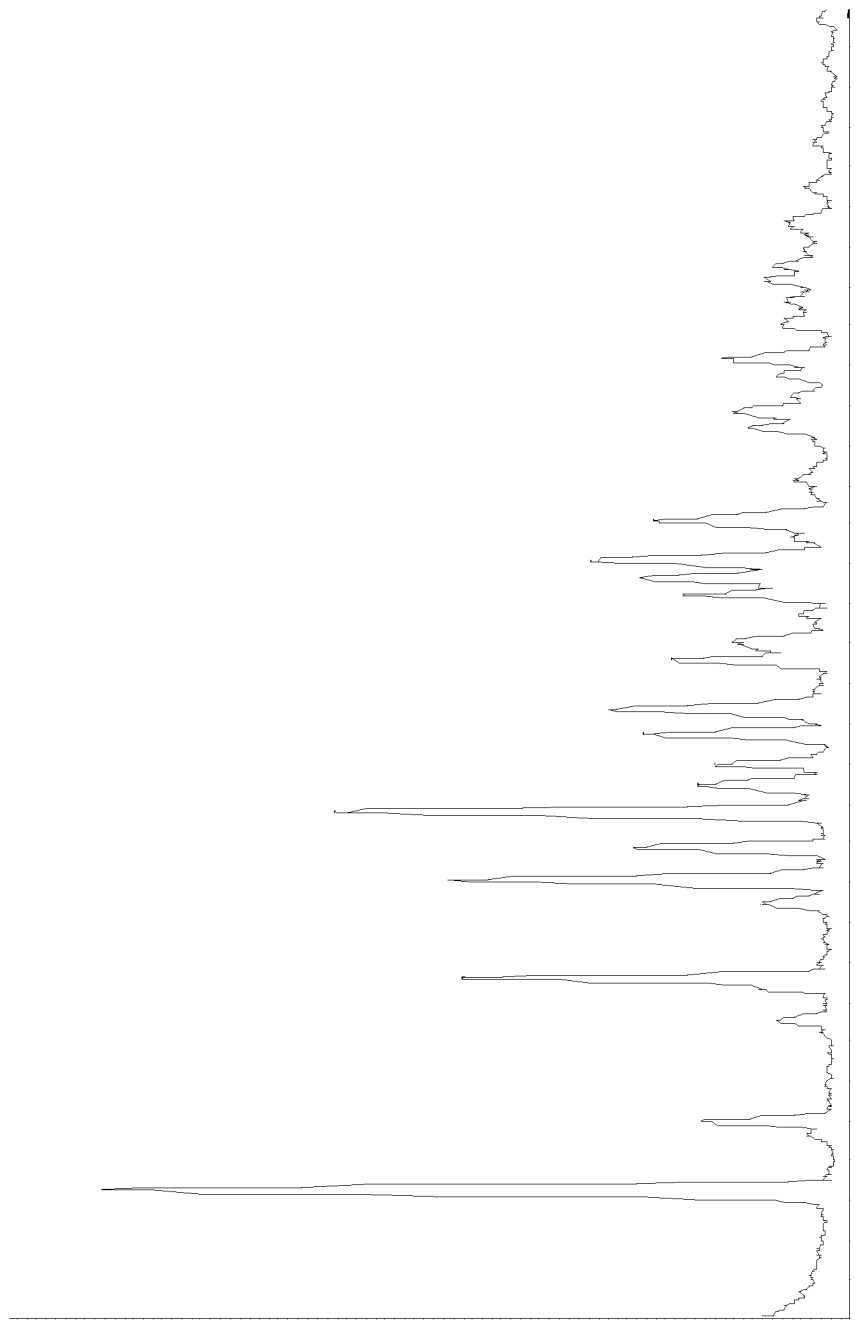
FIG. 1 is an XRPD scan of a sample of commercial everolimus converted to crystalline form.
Figure 2:
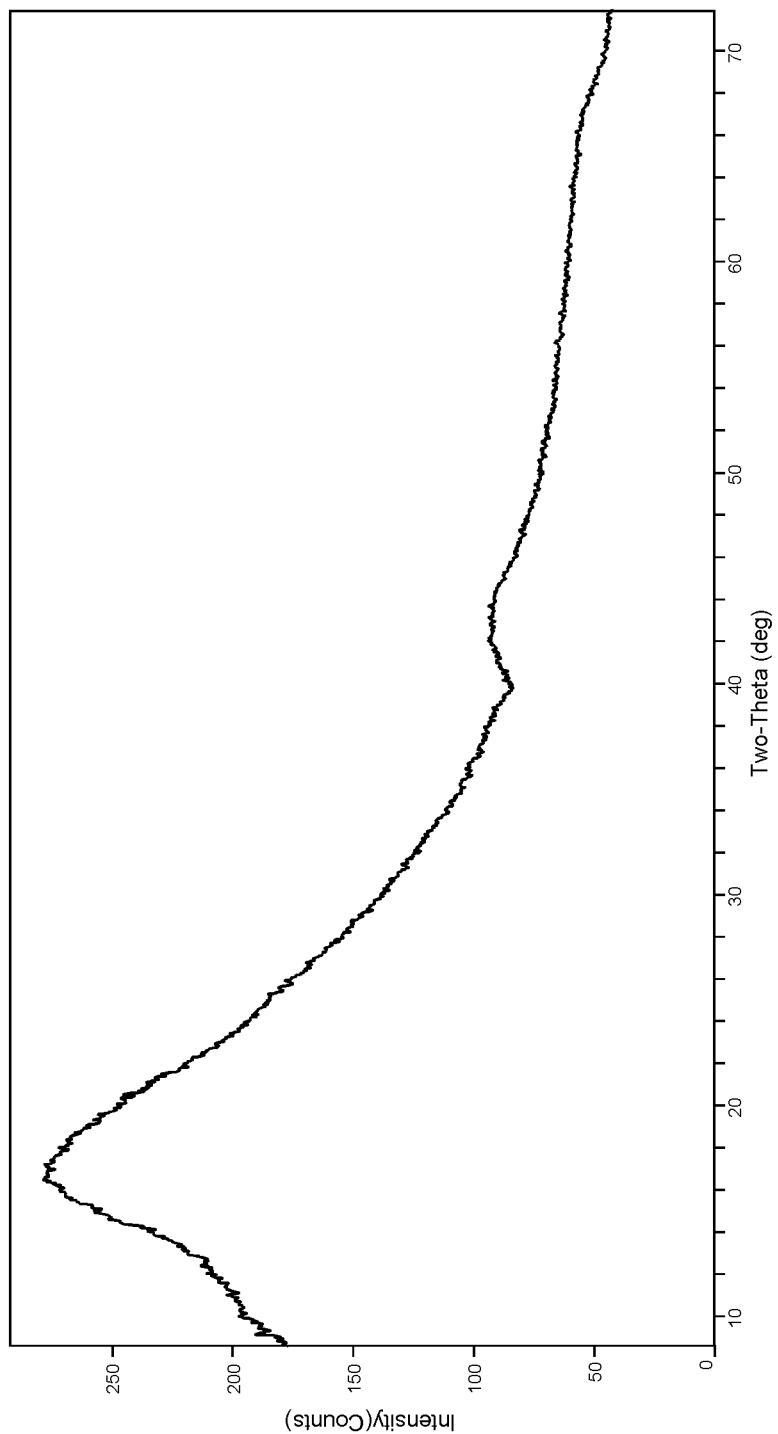
FIG. 2 is an X-ray powder (XRPD) scan of a sample of commercial everlolimus.

Referring to FIGS. 1 and 2, it can be seen that the XRPD scans of the respective crystalline and amorphous forms of everolimus are distinctly different. The crystalline form provides sharp characteristic peaks whereas the amorphous form has very broad indistinct features. Crystalline everolimus also shows birefringence under optical microscope using polarized lighting.

Figure 3:
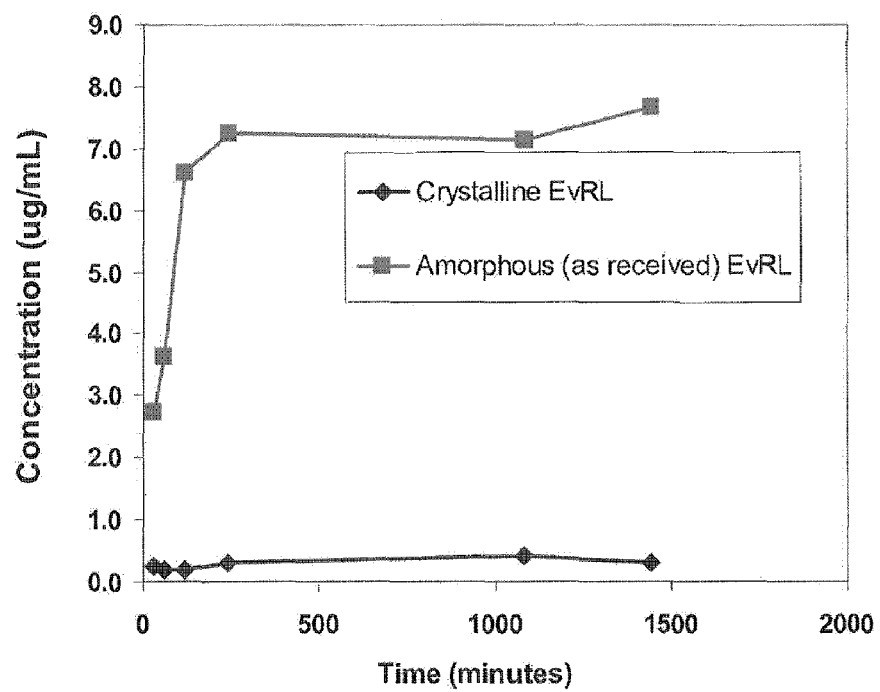
FIG. 3 is a graph showing the relative water solubilities of the amorphous and crystalline forms of everolimus.

The comparative aqueous solubilities of the two drug forms at body temperature (37° C.) is shown in FIG. 3.

The solubility of the amorphous form contributes to its bioavailability. However, when deployed at a specific site for prevention of restenosis it would be advantageous to be in a form that provides extended release without having to add polymer or other excipients which can contribute to an inflammatory response in some individuals. The much lower solubility of the crystalline form may provide such benefits.

The inventive method can also be used for conversion between forms of other drugs that have amorphous and crystalline forms.

In some embodiments, the drug may be a macrolide immunosuppressive (limus) drug. In some embodiments, the macrolide immunosuppressive drug is rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl]-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), or derivative, isomer, racemate, diastereoisomer, prodrug, hydrate, ester, or analog thereof, provided that the particular drug is one that has both an amorphous form and a crystalline form.

In some embodiments, the drug to be converted may be an amorphous form of everolimus, sirolimus, zotarolimus and biolimus. In some embodiments the drug is amorphous everolimus.

Other drugs for which the inventive conversion method that may be useful include antiinflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; and growth factors, again provided that the particular drug is one has an amorphous form and a crystalline form.

In some embodiments the invention is directed to slurry conversion of the drug from amorphous to crystalline form. Slurry conversion reduces the amount of solvent that is needed to obtain conversion of a given mass of the drug and reduces the energy budget for recovery of the crystalline drug, compared to a nucleated solution technique. To recover crystalline drug from solution one typically must induce nucleation, for instance by seeding, of a supersaturated solution, often requiring heating to fully dissolve the drug and then cooling the solution or evaporating the solvent. If the solvent is to be evaporated and recovered additional energy is needed for the recovery.

In the inventive conversion method some of the same factors in the solvent handling are still involved. However, because the mass of drug is never fully dissolved the energy budget for solvent heating, cooling and recovery can be proportionally reduced. Further, if evaporation is used in the course of the process, the lower amount of solvent evaporated can significantly reduce the potential for environmental disruption and/or worker exposure to the solvent.

The choice of solvent or solvent mixture is not particularly critical. The solubility should not be so high that substantial amount of the drug is substantially all dissolved before the slurry is formed. If most of the drug is dissolved there may be little benefit to the slurry conversion process. Typical techniques for crystallization from a solution will have to be utilized for recovery of the dissolved drug. In at least some embodiments the amount of solvent used will be an amount that will dissolve no more than about 50%, of the saturation amount, that is the amount of solvent needed to dissolve the mass of drug employed in any particular batch being converted. In some embodiments the amount of solvent used will be no more than about 30% of the saturation amount. For instance the amount may be from about 0.5% to about 25%, or from about 1% to about 20%, or from about 5% to about 15% of the saturation amount. In some embodiments no more than 30%, no more than 25%, no more than 20% or no more than 10% of the amorphous drug is soluble in the amount of solvent provided at the temperature of aging. In some embodiments from about 0.5% to about 50%, from about 1% to about 30% or from about 2% to about 20% of the drug is soluble in the volume of solvent provided at the temperature of aging.

The solubility should not be so low that the conversion rate is impractical. Slurry conversion is a process that depends on exchange of drug molecules between solid and liquid solution phases. In some cases solvent blends can be used to provide a suitable balance between conversion speed and saturation excess. Examples of solvents that may be used include alcohols such as methanol, ethanol (EtOH), isopropanol (IPA), n-butanol, isobutyl alcohol or t-butyl alcohol; acetonitrile (ACN); ethers such as tetrahydrofuran (THF) isopropyl ether (IPE), diethyl ether (DEE); ketone solvents such as acetone, 2-butanone (MEK), or methyl isobutyl ketone (MIBK); halogenated solvents such as dichloromethane (DCM), monofluorobenzene (MFB), α,α,α-trifluorotoluene (TFT), nitromethane (NM), ethyl trifluroacetate (ETFA); aliphatic hydrocarbons such as hexane, heptane, or the like; aromatic hydrocarbons, such as toluene or xylenes; and ester solvents such as ethyl acetate. Mixed solvents, for instance heptane/ethyl acetate, acetone/water, IPA/water, or IPA/THF, THF/heptane can also be used. In some embodiments the solvent is a mixture of an aliphatic hydrocarbon and an ether or ester cosolvent having a volume ratio in the range of from about 40:1 to about 5:1.

The temperature range for conducting the conversion can be any temperature below the boiling point of the solvent or temperature at which the drug begins to show thermal degradation. For instance, for a drug such as everolimus, a suitable temperature may be in the range of from about −30° C. to about 60° C., or from 4° C. to 50° C. In some cases it may accelerate conversion to initially supersaturate the slurry, by cooling a solution after it has been saturated at or above ambient. In other cases effective conversion can be accomplished with an ambient temperature aging.

To accelerate the conversion, the saturated slurry may be cooled or some of the solvent evaporated to force formation of seed crystals in of the drug. In some cases seed crystals of the crystalline drug form may be added to the slurry to speed initiation of conversion. Without being bound thereto, it is believed the seed crystals will grow over time as amorphous drug is dissolved and then is removed from the solution by addition to the existing seed crystals. Over time substantially all of the solid amorphous drug is replaced with crystalline drug.

In the case of a drug that has more than one crystalline form, the addition of seed crystals of a desired crystalline form may allow better control of the crystalline form obtained by the inventive process In some embodiments intermittent or continuous agitation may accelerate the conversion process by breaking crystals to form more seed area and by maximizing the efficiency of dissolution of the amorphous drug as crystal formation removes the drug from solution. Agitation may be accomplished by sonication, stirring, shaking or the like. Particular conditions of agitation may also provide a specific particle size range of the crystalline drug product.

The skilled person can determine a suitable aging time taking into account the particular combination of drug and solvent used, the relative amounts of those ingredients, the temperature(s) employed and the other conditions employed, as well as the desired degree of conversion. In at least some embodiments the aging time will be sufficient to provide conversion of the amorphous drug to at least 50%, at least 75%, at least 80%, at least 85%, or at least 90% of the mass to crystalline form. Aging times for instance may be from about 1 day to about 15 days or more, or from about 2 to about 7 days, or from about 4-6 days.

At the end of the conversion the solids may be separated from the solvent, for instance by filtration, centrifuging or decanting, and then the solids dried. In some cases separate solvent/drug solution may be combined with additional amorphous drug in a semi-continuous or sequential batch conversion process. Alternatively all of the solvent may be removed by evaporation or heating, optionally with solvent recovery for instance by cooling the solvent vapor downstream of the slurry.

In embodiments using amorphous everolimus, conversion of the amorphous drug to a 85-98% crystalline form drug is obtained with little or no change in drug purity. If the solvent is fully removed from the mass by evaporation, the purity generally should not be affected. If the solvent is separated before drying there may be some increase in purity over the starting drug.

If the drug includes a stabilizer component, in some case the minor amount of the stabilizer in the drug may change enough to influence the stability of the crystalline drug. Consequently stabilizer retention in the crystalline product should be separately confirmed and adjusted if needed.

In some embodiments a stabilizer component provided in the amorphous drug, such as butylated hydroxy toluene (BHT) or another antioxidant stabilizer, may be substantially removed by the conversion process of the invention, e.g. if the crystalline drug is separated from the solvent by filtration, decanting, centrifugation or the like. This may be desirable for drug coated medical devices since a stabilizer itself may be a source of tissue inflammation on the device. If the coating process and coated devices are protected from oxygen until the time of use adequate shelf life can be achieved without stabilizer. This may be accomplished for instance, by processing crystalline everolimus under nitrogen or another inert gas during isolation and coating process, and then packaging the coated device in an air-tight enclosure that has been filled with inert gas. In some embodiments therefore the invention pertains to a medical device coated with a crystalline drug, such as crystalline everolimus, that is substantially free (e.g. less than 0.1%, or less than 0.01%) of antioxidant stabilizer, or one in which the amount of stabilizer has been reduced by more than 50%, for instance more than 70%, more than 80% or more than 90% from a commercial amorphous form of the drug.

In some embodiments for applying a crystalline drug to a medical device, a suspension of crystalline particles is applied, optionally with a non-polymeric excipient that facilitates bonding or film formation, without dissolving the drug, and the suspension vehicle evaporated to provide a polymer-free crystalline drug coating.

Exemplary non-polymeric excipients include citrate esters, such as acetyl tributyl citrate or other acetylated trialkyl citrates, trialkyl citrates, and trialkyl citrates that have been etherified at the hydroxyl group on citric acid. Other non-polymeric excipients that may be useful include surfactants such as described in US 2008/0118544 A1; oils; esters of fatty acids and $C_1$-$C_6$ alcohols such as isopropyl myristate; triacetin; and the like. Other documents in which describe non-polymeric excipients that may be useful include US 2005/0101522 A1; US 2006/0020243 A1; US 2008/0255509 A1; US 2010/0063585 A1; US 2010/0179475 A1; and US 2010/0272773 A1. In at least some embodiments the excipient is selected to be one in which the drug is substantially undissolved, so that the major portion of the drug remains in the crystalline form.

The medical devices used in conjunction with the present invention include any device amenable to the coating processes described herein. The medical device, or portion of the medical device, to be coated or surface modified may be made of metal, polymers, ceramics, composites or combinations thereof. Whereas the present invention is described herein with specific reference to a vascular stent, or balloon other medical devices within the scope of the present invention include any devices which are used, at least in part, to penetrate the body of a patient. Non-limiting examples of medical devices according to the present invention include catheters, guide wires, balloons, filters (e.g., vena cava filters), stents, stent grafts, vascular grafts, intraluminal paving systems, soft tissue and hard tissue implants, such as orthopedic repair plates and rods, joint implants, tooth and jaw implants, metallic alloy ligatures, vascular access ports, artificial heart housings, artificial heart valves, aneurysm filling coils and other coiled coil devices, trans myocardial revascularization ("TMR") devices, percutaneous myocardial revascularization ("PMR") devices, hypodermic needles, soft tissue clips, holding devices, and other types of medically useful needles and closures, and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like. Any exposed surface of these medical devices may be coated with the methods and apparatus of the present invention.

In at least some embodiments the drug crystals in such a coating have a mean particle size of less than about 100 μm as measured by dynamic light scattering methods, for instance using photocorrelation spectroscopy, laser diffraction, low angle laser light scattering (LALLS), medium-angle laser light scattering (MALLS), light obscuration methods (Coulter method, for example), rheology, or microscopy (light or electron). The particles can be prepared in a wide range of sizes, such as from about 20 μm to about 10 nm, from about 10 μm to about 10 nm, from about 2 μm to about 10 nm, from about 1 μm to about 10 nm, from about 400 nm to about 50 nm, from about 200 nm to about 50 nm or any range or combination of ranges therein. The crystalline particle size in some cases may be sized to a desired distribution using agitation methods such as sonication during slurry aging. Alternatively a desired particle size may be obtained by mechanical grinding techniques such as pearl milling, a ball milling, hammer milling, fluid energy milling or wet grinding techniques or the like after the drug has been converted to crystalline form.

In specific examples slurries of everolimus may be prepared by adding enough solids to a given solvent at ambient conditions so that undissolved solids are present. The mixture may then be loaded onto a digital oscillator, stir plate or rotating wheel in a sealed vial at ambient or elevated temperature for an extended period of time, typically from 1 to 7 days. The solids may be isolated by vacuum filtration or by decanting the liquid phase and allowing the solid to air dry in an open vial at ambient conditions, or drying under nitrogen at ambient or another suitable temperature.

In other examples, mixtures with undissolved solids of solvent and everolimus may be left to stand under ambient conditions. Solids are collected by vacuum filtration or by decanting the solvent and air drying at ambient conditions or under nitrogen.

The invention is illustrated by the following non-limiting examples.

EXAMPLES

Approximate solubilities of amorphous everolimus were determined by adding the drug gradually with stirring at room temperature to a fixed volume of the solvent until solid remained visible. Results are shown in Table 1.

TABLE 1

| Solvent(s) | Amorphous Everolimus Solubilities mg/mL |
|---|---|
| Acetone | ~100 |
| ACN | ~100 |
| DCM | ~46 |
| DMF | ~49 |
| p-dioxane | ~58 |
| EtOH | ~100 |
| ethyl acetate | ~100 |
| n-heptane | ~0.5 |
| hexanes | not measured |
| IPA | ~15 |
| MEK | ~70 |
| MTBE | ~62 |
| THF | ~67 |
| water | ~0.1 |
| m-xylene | ~76 |
| ACN/water 3:2 v/v | ~52 |
| DMF/DCM w/w | ~142 |
| DMF/EtOAc w/w | ~119 |
| DMF/THF w/w | ~112 |

Typically the solubility can be expected to increase from these values at higher than ambient temperatures and decrease at lower than ambient temperatures. The rates of change with temperature, however, may be quite different between different solvent systems.

Examples 1-3 and 5

A supersaturated slurry suspension of amorphous everolimus in an organic cosolvent solution was prepared. The slurry was aged at 50° C. while agitating in an orbital shaker set to 120 rpm for a couple of days. Some solvent evaporated under these conditions. The slurry is then placed at 4° C. for several days to allow for crystal growth as well as additional solvent evaporation.

Example 4

Another everolimus crystalline sample was prepared by adding to approximately 500 mg of purified amorphous everolimus, 500 µL of a 1:20 ethyl acetate/heptane solvent solution. A slurry suspension was generated. The slurry was incubated uncovered at ambient conditions overnight to allow for complete solvent evaporation. The product had a crystalline habit that was seen to be a combination of larger needles and plate like crystals when observed under the polarized light microscope Example 6

Approximately 200 mg of amorphous everolimus was added to 500 µL of isopropanol. The slurry solution was then briefly vortexed and incubated, with the crystallization vessel covered, at ambient conditions for two days. The solvent was then allowed to completely evaporate. The product had a needle-like crystalline habit when observed under a polarized light microscope. Analysis by HPLC of the purity of the recovered crystalline everolimus was 91.4%.

Example 7

Crystals of sample everolimus were generated dissolving approximately 100 mg of amorphous everolimus in 500 µL of p-xylene. A slurry suspension was then generated by adding additional everolimus. The slurry suspension was vortexed and incubated at ambient conditions for an extended period of time. The slurry was allowed to evaporate for several days the following incubation period. Microscopic inspection of the product showed a micro-crystalline structure exhibiting a needle-like habit when observed under a polarized light.

Table 2 contains further details of these examples and the products obtained. "EvRL" designates everolimus.

TABLE 2

Summary of Solvent Systems Used to Generate Crystalline Everoliumus

| Example No. | Solvent System | Weight of EvRL per volume solvent solution (w/v) | EvRL Conc. (mg/mL) | Conditions | Total mix/dry time | Birefringence Observed |
|---|---|---|---|---|---|---|
| 1 | 1:20 EtOAc:Heptane slurry | 97 mg in 500 µL solution | 194 mg/mL | 1) 50° C. orbital shaker (120 rpm) for 2 days 2) Store at 4° C. for 4 days 3) Left uncovered overnight for additional solvent evaporation | ~6 days | Yes |

TABLE 2-continued

Summary of Solvent Systems Used to Generate Crystalline Everoliumus

| Example No. | Solvent System | Weight of EvRL per volume solvent solution (w/v) | EvRL Conc. (mg/mL) | Conditions | Total mix/dry time | Birefringence Observed |
|---|---|---|---|---|---|---|
| 2 | 1:20 EtOAc:Heptane slurry | 92 mg in 500 µL solution | 184 mg/mL | 1) 50° C. orbital shaker (120 rpm) for 6 days [note: solvent had fully evaporated within 6 day shaking time] | ~6 days | Yes |
| 3 | 1:10 EtOAc:Heptane slurry | 109 mg in 1000 µL solution | 109 mg/mL | 1) 50° C. orbital shaker (120 rpm) for 2 days 2) Store at 4° C. for 4 days 3) Left uncovered overnight for additional solvent evaporation | ~6 days | Yes |
| 4 | 20:1 EtOAc:Heptane slurry | 496 mg EvRL in 500 µL solution | 992 mg/mL | 1) Fast evaporation (allowed to dry uncovered) 2) Left uncovered overnight for additional solvent evaporation | ~1 day | Yes |
| 5 | 1:40 THF:Heptane slurry | 95 mg EvRL in 500 µL solution | 190 mg/mL | 1) 50° C. orbital shaker (120 rpm) for 2 days 2) Store at 4° C. for 4 days 3) Left uncovered overnight for additional solvent evaporation | ~6 days | Yes |
| 6 | IPA slurry | 192 mg EvRL in 500 µL solution | 384 mg/mL | 1) Room temperature slurry for 2 days (no shaking) | ~2 days | Yes |
| 7 | p-xylene slurry | 411 mg EvRL in 500 µL solution | 822 mg/mL | 1) Slow evaporation (leave cover on, but unscrewed) 2) Left uncovered overnight for additional solvent evaporation | ~2 days | Yes |

In addition to the inventions recited in the claims other subject matter considered to be inventive disclosed herein includes the following items:

A. A medical device having a polymer-free coating comprising crystalline everolimus.

B. A medical device having a drug coating comprising crystalline everolimus which is substantially free of an antioxidant.

C. A medical device as in item A or B wherein the crystalline form everolimus comprises at least 85% by weight of the drug.

D. A medical device as in claim Item B wherein the crystalline form everolimus comprises at least 90% by weight of the drug.

E. A medical device as in item A or B wherein the polymer-free coating comprises a mixture of crystalline and amorphous everolimus, the mixture comprising from 15% to 90% by weight of said crystalline everolimus.

F. A medical device as in one of items A-E wherein the device is stent, a catheter balloon, guide wire, heart valve, catheter, vena cava filter, vascular graft or a stent graft.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of converting an amorphous form of a drug to a crystalline form of said drug comprising the steps of
providing an amount of said drug in a solid amorphous form, the drug is everolimus;
providing a volume of a solvent for the drug, the solvent is selected from the group consisting of tetrahydrofuran/ heptane, tetrahydrofuran/ethyl acetate, isopropyl alcohol and p-xylene, the volume being insufficient to fully dissolve said amount of the drug, forming a slurry with said volume of said solvent and said amount of said drug; and aging the slurry for a time to allow substantial conversion of the solid amorphous drug into crystalline drug.

2. A method as in claim 1 wherein during at least a portion of the aging time the slurry is subjected to agitation.

3. A method as in claim 1 wherein the volume of said solvent is no more than 50%, the amount of solvent needed to fully dissolve said amount of the drug at the temperature of aging.

4. A method as in claim 3 wherein the volume of said solvent is no more than 30% of the amount of solvent needed to fully dissolve said amount of the drug at the temperature of aging.

5. A method as in claim 3 wherein the volume of said solvent is from about 2% to about 20% of the amount of solvent needed to fully dissolve said amount of the drug at the temperature of aging.

6. A method as in claim 1 wherein seed crystals of the crystalline drug form are be added to the slurry.

7. A method as in claim 1 wherein during said aging step the slurry is agitated in a manner that breaks formed crystals of the drug into a predetermined size distribution.

8. A method as in claim 1 wherein a mixture of two or more organic solvents are used as the solvent for the drug.

9. A method as in claim 1 wherein the slurry is aged at a temperature of from about 4° C. to about 80° C.

* * * * *